United States Patent
Larkin et al.

(10) Patent No.: US 9,683,912 B2
(45) Date of Patent: Jun. 20, 2017

(54) DRIVE SIGNAL DISTRIBUTION FOR DIRECT FIELD ACOUSTIC TESTING

(71) Applicants: Paul Larkin, Mt. Airy, MD (US); Arthur Isaacs, Columbia, MD (US); Michael Sullivan, Eldersburg, MD (US)

(72) Inventors: Paul Larkin, Mt. Airy, MD (US); Arthur Isaacs, Columbia, MD (US); Michael Sullivan, Eldersburg, MD (US)

(73) Assignee: MSI DFAT LLC, Baltimore, MD (US)

( * ) Notice: Subject to any disclaimer, the term of this patent is extended or adjusted under 35 U.S.C. 154(b) by 358 days.

(21) Appl. No.: 14/354,483

(22) PCT Filed: Oct. 26, 2012

(86) PCT No.: PCT/US2012/062255
§ 371 (c)(1),
(2) Date: Apr. 25, 2014

(87) PCT Pub. No.: WO2013/063491
PCT Pub. Date: May 2, 2013

(65) Prior Publication Data
US 2014/0298912 A1    Oct. 9, 2014

Related U.S. Application Data

(60) Provisional application No. 61/552,081, filed on Oct. 27, 2011.

(51) Int. Cl.
*G01M 7/00* (2006.01)
*G01N 29/14* (2006.01)
(Continued)

(52) U.S. Cl.
CPC .............. *G01M 7/00* (2013.01); *G01N 29/14* (2013.01); *G01N 29/4427* (2013.01); *G01N 29/46* (2013.01)

(58) Field of Classification Search
CPC .... G01N 29/14; G01N 29/4427; G01N 29/46; G01N 29/04; G01M 7/00
See application file for complete search history.

(56) References Cited

U.S. PATENT DOCUMENTS

| 4,989,158 A | 1/1991 | Sloane |
| 5,138,884 A | 8/1992 | Bonavia |

(Continued)

FOREIGN PATENT DOCUMENTS

| CN | 101609068 A | 12/2009 |
| CN | 101699236 A | 4/2010 |

(Continued)

OTHER PUBLICATIONS

Larkin, et al., "Recent Developments in Direct Field Acoustic Testing", 26$^{TH}$ Soace Simulation Conference 2010: Annapolis, Maryland, USA, Oct. 18-21, 2010, pp. 465-492.

(Continued)

*Primary Examiner* — Paul West
*Assistant Examiner* — Xin Zhong
(74) *Attorney, Agent, or Firm* — Medler Ferro; Woodhouse & Mills PLLC (57) ABSTRACT

A direct field acoustic testing system provides an acoustic field having a higher degree of spatial uniformity. The system includes a control microphone, a controller, a combiner, and at least four acoustic transducers. The controller is operatively coupled to the control microphone such that the controller receives at least one input signal from the control microphone and provides at least four separately controllable controller output signals. The combiner com- (Continued)

bines the at least four separately controllable output signals to form at least four secondary output signals, each composed of combinations of one or more of the at least four separately controllable controller output signals. Each of the at least four transducers is operatively coupled to at least one of the at least four secondary output signals such that the output of the transducer varies in response to changes in at least two of the at least four separately controllable controller output signals.

13 Claims, 11 Drawing Sheets

(51) Int. Cl.
  *G01N 29/44* (2006.01)
  *G01N 29/46* (2006.01)

(56) References Cited

U.S. PATENT DOCUMENTS 5,299,459 A    4/1994  Underwood
5,638,004 A    6/1997  Combs et al.
6,591,226 B1   7/2003  Hartmann et al.
6,668,650 B1 * 12/2003 Lafleur .................. G01M 7/00
                                                73/571
2001/0032510 A1* 10/2001 Eagen ..................... G01M 7/00
                                                73/571
2003/0108208 A1  6/2003  Thomas et al.
2004/0024750 A1  2/2004  Ulyanov et al.
2004/0216524 A1* 11/2004  Lafleur .................. G01M 7/00
                                                73/579

FOREIGN PATENT DOCUMENTS

WO        01/01103 A1    1/2001
WO     2012/166688 A1   12/2012

OTHER PUBLICATIONS

Rouse, et al., "Analytical Modeling of the Acoustiv Field During a Direct Field Acoustic Test", Journal of IEST / Institue of Environmental Sciences and Technology, IEST, vo. 54, No. 2, Oct. 1, 2011, pp. 1-53.

* cited by examiner

Assignment of Controller Outputs to Transducer Groups

| Transducer Groups | Mid and HF Transducers | | | | | | | | | LF Transducers | | |
|---|---|---|---|---|---|---|---|---|---|---|---|---|
| | 1 | 2 | 3 | 4 | 5 | 6 | 7 | 8 | 9 | 10 | 11 | 12 |
| Controller Outputs | | | | | | | | | | | | |
| 1 | X | | | | | | | | | | | |
| 2 | | X | | | | | | | | | | |
| 3 | | | X | | | | | | | | | |
| 4 | | | | X | | | | | | | | |
| 5 | | | | | X | | | | | | | |
| 6 | | | | | | X | | | | | | |
| 7 | | | | | | | X | | | | | |
| 8 | | | | | | | | X | | | | |
| 9 | | | | | | | | | X | | | |
| 10 | | | | | | | | | | X | | |
| 11 | | | | | | | | | | | X | |
| 12 | | | | | | | | | | | | X |

Improved Assignment of Controller Outputs to Transducer Groups

| Transducer Groups | Mid and HF Transducers | | | | | | | | | LF Transducers | | |
|---|---|---|---|---|---|---|---|---|---|---|---|---|
| Controller Outputs | 1 | 2 | 3 | 4 | 5 | 6 | 7 | 8 | 9 | 10 | 11 | 12 |
| 1 | X | | | X | | | X | | | X | | |
| 2 | | X | | | X | | | X | | | X | |
| 3 | | | X | | | X | | | X | | | X |
| 4 | X | | | X | | | X | | | X | | |
| 5 | | X | | | X | | | X | | | X | |
| 6 | | | X | | | X | | | X | | | X |
| 7 | X | | | X | | | X | | | X | | |
| 8 | | X | | | X | | | X | | | X | |
| 9 | | | X | | | X | | | X | | | X |
| 10 | X | | | X | | | X | | | X | | |
| 11 | | X | | | X | | | X | | | X | |
| 12 | | | X | | | X | | | X | | | X |

DRIVE SIGNAL DISTRIBUTION FOR DIRECT FIELD ACOUSTIC TESTING

CROSS-REFERENCE TO RELATED APPLICATIONS

The present application is a non-provisional application claiming the benefit under 35 U.S.C. §119(e) of U.S. Provisional Patent Application No. 61/552,081 filed Oct. 27, 2011, which is hereby incorporated by reference in its entirety herein.

BACKGROUND OF THE INVENTION

Field of the Invention

The present invention relates generally to the field of vibration testing of objects such as satellites, instrumentation or any other object whose reliability in operation may be evaluated using high intensity vibration testing. Specifically, the present invention relates to the use of direct field acoustic systems to perform vibration testing and to control means to allow direct field acoustic systems to produce a an acoustic field conforming to a predetermined specification.

Background of the Invention

The specification of co-pending U.S. application Ser. No. 13/117,870, filed May 27, 2011 titled Direct Field Acoustic Testing System and Method (hereinafter "the '870 application") is incorporated by reference herein. As discussed in the '870 application, in the field of Direct Field Acoustic Testing (DFAT) it is generally desirable to obtain an acoustic field having a uniform spectral content throughout the space around the Unit Under Test (UUT). As demonstrated in the '870 application excellent spectral uniformity was obtained at the control microphone locations through the use of a Multiple-Input-Multiple-Output (MIMO) arrangement incorporating multiple groups of independently controllable acoustic transducers. However, monitoring of the acoustic field with additional non-control or monitoring microphones has shown that while spectral variations are well controlled at the control locations, greater variations and deviations from specification exist at non-control locations. A general shift to higher acoustic intensities at the non-control locations has also been observed for frequencies generally above 150 Hz leading to a risk of over testing the UUT. It is therefore advantageous to provide an enhanced DFAT system which reduces these variations and maintains a closer correspondence between the spectral acoustic magnitude response at control and non-control locations.

SUMMARY OF THE INVENTION

Embodiments hereof include a direct field acoustic testing system with at least four groups of acoustical transducers, at least four separately controllable controller output signals and a signal modifier and combiner for modifying and directing combinations of controller output signals to each group of acoustical transducers so as to provide an acoustic field having a higher degree of spatial uniformity.

Embodiments hereof also include a direct field acoustic testing system with at least one microphone disposed in an appropriate location to provide at least one acoustical input signal which is used to determine the separately controllable controller output signals, at least four groups of acoustical transducers and a signal modifier and combiner for modifying and directing combinations of controller output signals to each group of acoustical transducers so as to provide an acoustic field having a higher degree of spatial uniformity.

Embodiments hereof also include a direct field acoustic testing system, at least one control microphone, a multiple-input-multiple-output (MIMO) vibration control system having at least one input and at least four separately controllable controller outputs, at least four separately driven groups of acoustical transducers and a signal modifier and combiner for modifying and directing combinations of separately controllable controller output signals to each of the at least four separate groups of transducers so as to provide an acoustic field having a higher degree of spatial uniformity.

Embodiments hereof also include a direct field acoustic testing system with at least one microphone disposed in an appropriate location to provide at least one acoustical input signal which is used to determine the separately controllable controller output signals, at least four groups of acoustical transducers disposed in an approximately circular arrangement and a signal modifier and combiner for modifying and directing combinations of controller output signals to each of the at least four groups of acoustical transducers wherein at least two of the separately controllable controller output signals are each directed to at least two groups of acoustical transducers in such a way as to provide an approximately even distribution of said at least two separately controllable controller output signals within the test environment so as to provide an acoustic field having a higher degree of spatial uniformity.

Embodiments hereof also include a direct field acoustic testing system, at least one control microphone, a multiple-input-multiple-output (MIMO) vibration control system having at least one input and at least four separately controllable controller output signals, at least four separately driven groups of acoustical transducers and a signal modifier and combiner for modifying and directing combinations of separately controllable controller output signals to each of the at least four separate groups of transducers such that the output of at least one separate group of transducers varies in response to changes in at least two of the separately controllable controller output signals.

BRIEF DESCRIPTION OF THE DRAWINGS

Embodiments of the invention will now be described, by way of example only, with reference to the accompanying schematic drawings in which corresponding reference symbols indicate corresponding parts.

DETAILED DESCRIPTION OF EMBODIMENTS OF THE INVENTION

Embodiments hereof are now described with reference to the figures where like reference characters/numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention.

Figure 1:
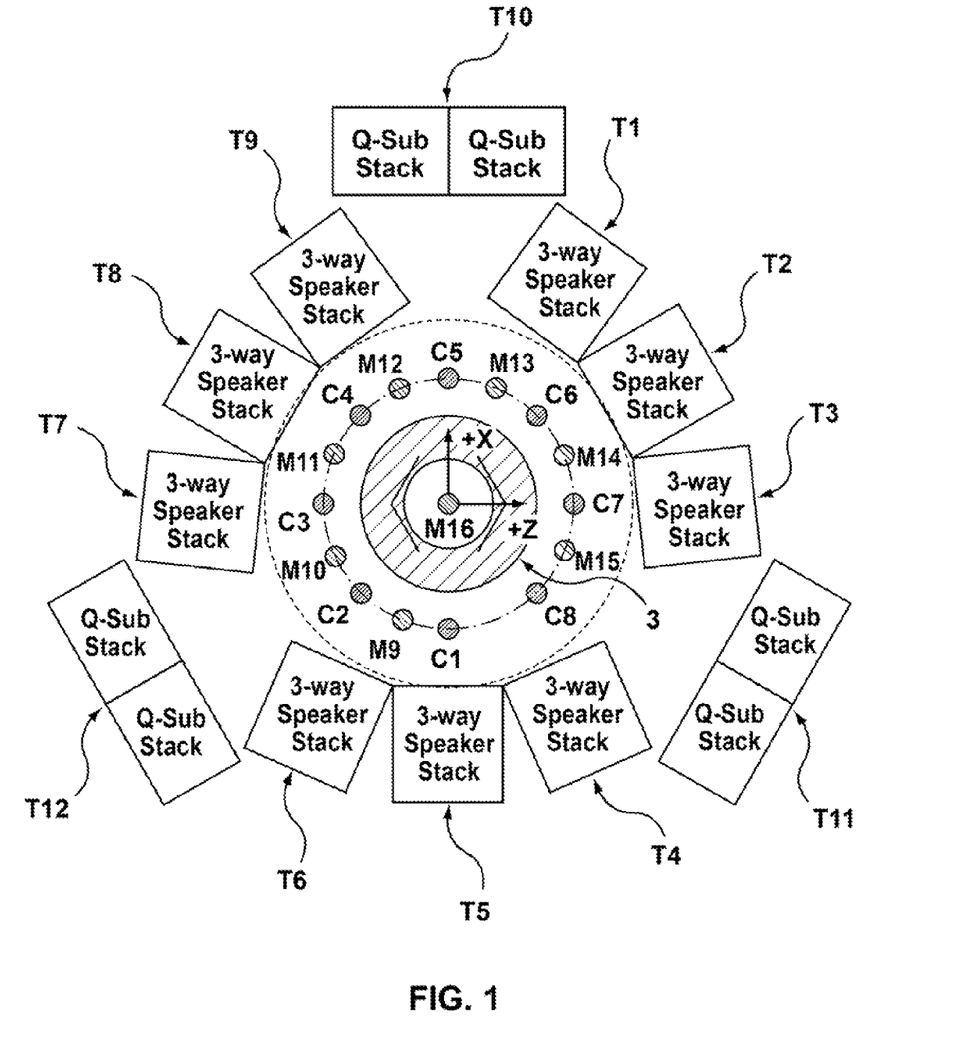
FIG. 1 schematic layout of an acoustical transducer group for direct field acoustic testing according to the '870 application.

Referring to FIG. 1, an embodiment of a DFAT system in accordance with co-pending U.S. application Ser. No. 13/117,870, filed May 27, 2011 ("the '870 application) is shown. Included is a transducer array composed of electro-dynamic acoustic sources or transducers T1-T12 covering various frequency ranges arrayed around the unit-under test (UUT) 3 in a generally circular arrangement as shown. The transducer array in the embodiment shown is composed of twelve groups T1-T12 of eight transducers, of which nine groups T1-T9 are three-way electro-dynamic loudspeaker systems generally covering the frequency range above 100 Hz and three groups T10-T12 are electro-dynamic sub-woofer loudspeakers generally covering the frequency range from 20 Hz to 200 Hz. Control microphones C1-C12 are disposed at various positions around the UUT 3 for the purpose of providing information about the acoustic field to a control system (described below). Monitoring microphones M9-M16 may also be provided for monitoring the acoustic field at specific points of particular interest during operation but are not essential to the operation of this or any other embodiment hereof. Monitoring microphones may be located anywhere in the acoustic test space and need not correspond to control microphone locations.

Figure 2:
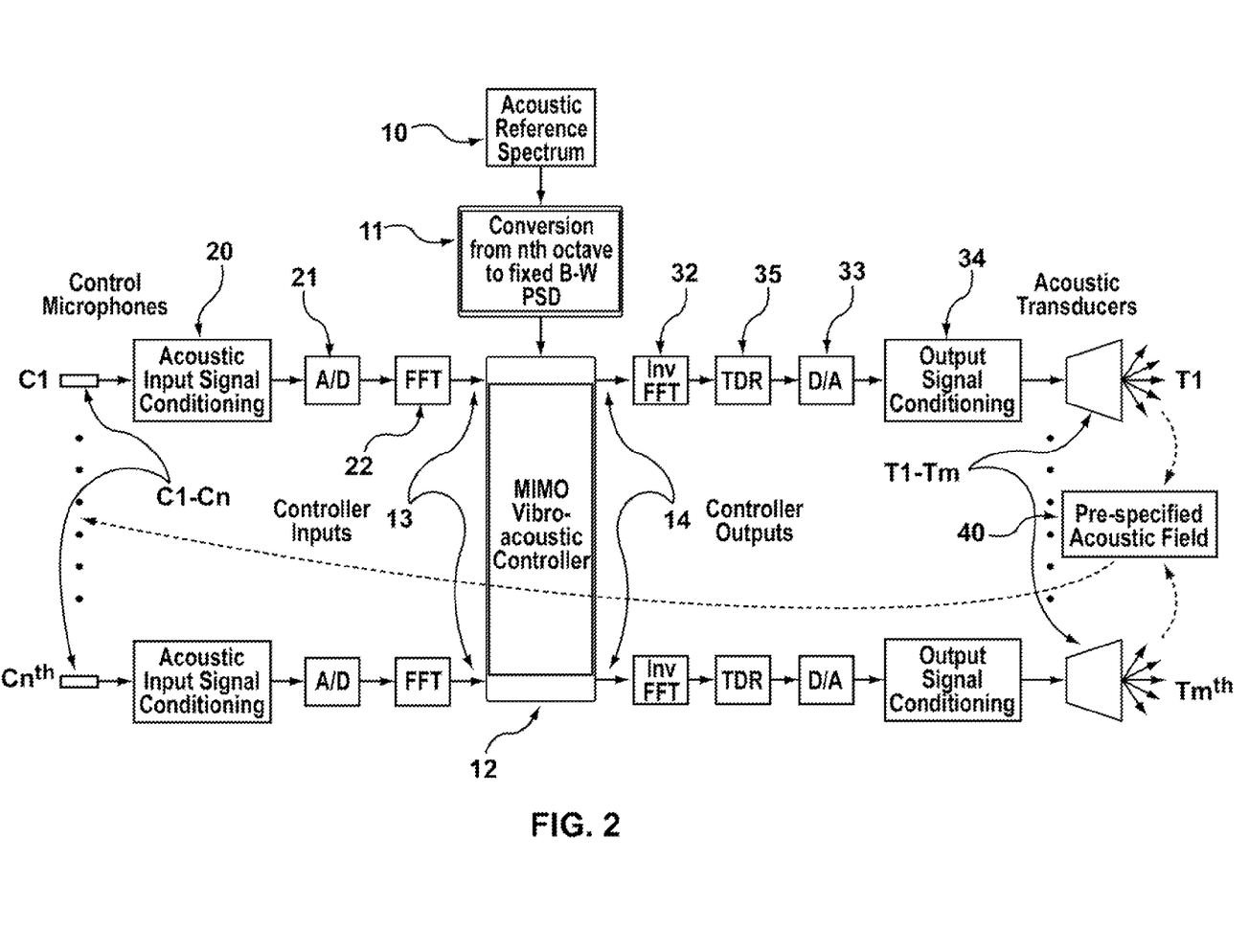
FIG. 2 is simplified block diagram of a direct field acoustic testing system according to the '870 application.

Referring to FIG. 2, a simplified block diagram of the DFAT system of FIG. 1 in accordance with the '870 application is shown. Each of the control microphones C1-Cn produces electrical signals which are representative of the acoustic field at each microphone. Each of the electrical signals is conditioned in an input signal conditioner 20 according to the input requirements of a vibro-acoustic controller 12. By way of example and not of limitation, conditioner 20 may include anti-aliasing or other filters, application of microphone calibration data referenced to appropriate standards, and scaling of the signal to represent the proper units. An analog to digital converter 21 converts the conditioned electrical signals to a digital format and the digitized signals are converted to fixed band-width narrow-band power spectral densities by application of a Fast Fourier Transform (FFT), as represented in block 22 of FIG. 2. Each of these resulting data streams is connected to one input 13 of the vibro-acoustic controller 12. Those of ordinary skill in the art recognize that the input signal conditioner 20, ND converter 21, and the FFT 22 may be part of the controller 12. Each output 14 from the controller 12 is converted from a narrow-band power spectral density to a digitized time series by an inverse FFT, as represented in block 32. This digitized time series may then be time domain randomized 35 depending on the type of test being conducted and then converted to an analog signal in digital to analog converter 33. Each analog signal is then conditioned in output signal conditioner 34 according to the input requirements of the amplification and acoustic transducers T1-Tm. By way of example and not of limitation, the conditioning may include additional filtering, gain, attenuation or power amplification. Each of the conditioned signals is then applied to the respective acoustical transducer group, T1-Tm. A pre-specified acoustical reference spectrum 10 is converted from the standard 1/nth octave format to a fixed band-width narrow-band power spectral density format which is consistent with the format of the signals from the control microphones C1-Cn and applied to the vibro-acoustic controller inputs 13. Those of ordinary skill in the art recognize that the inverse FFT 32, time domain randomization, the digital to analog converted 33, and the output signal conditioner may part of the controller 12.

Figure 3:
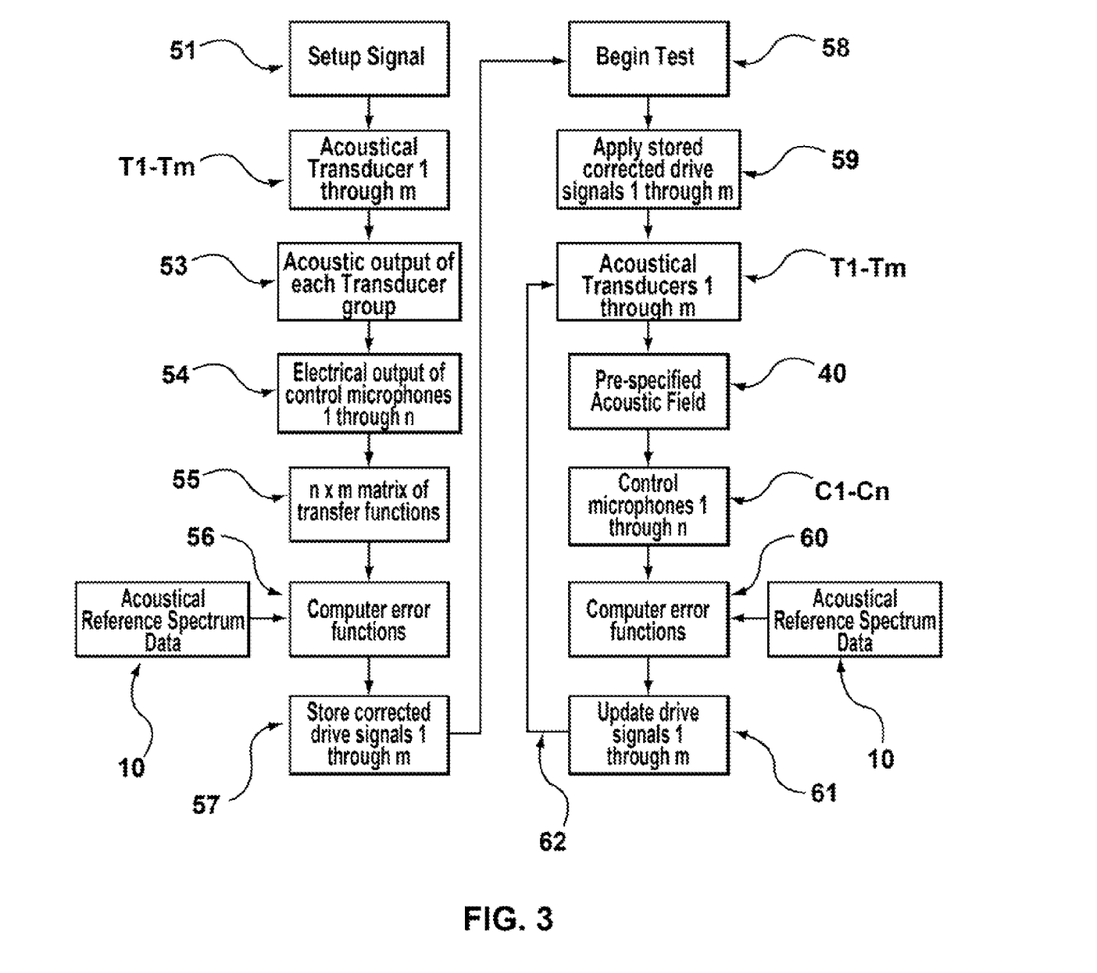
FIG. 3 is a simplified control diagram for the vibro-acoustic controller of the system of FIG. 2

The principles of multiple-input-multiple-output (MIMO) control logic will be familiar to those skilled in the art and may be applied in many different ways within the scope of the present invention in the implementation of this and other embodiments. Referring to FIG. 3, a simplified block diagram which describes generally the functioning of one possible embodiment of a MIMO vibro-acoustic controller 12 is shown which is in accordance with the '870 application. During the setup process a signal 51 is applied to each of the acoustical transducer groups T1-Tm. The acoustic output 53 of each transducer group is separately monitored by each control microphone C1-Cn. The electrical outputs of control microphones C1-Cn in response to each transducer group represent the transfer functions of each combination of transducer group and control microphone which are recorded in an n×m matrix 55 where each element is one such transfer function. These transfer functions are compared to the acoustical reference spectrum data 10. A matrix of error functions 56 is computed which is used to compute a corrected drive signal 57 for each of the transducer groups T1-Tm. At the start of the actual test 58 the previously stored 1 through m corrected drive signals 57 are applied 59 to the respective transducer groups T1-Tm. The resulting acoustic field is monitored by the control microphones C1-Cn and their outputs are compared to the acoustical reference spectrum data 10 from which error functions 60 are computed. These error functions 60 are used to provide real time updates of the drive signals 61 which are applied to through control loop 62 to the respective transducer groups T1-Tm. This embodiment may be operated in either closed loop control mode as shown in FIG. 3 or in open loop control mode. In open loop mode no real time adjustments to the drive signals are made after the initial application 59 of the stored corrected drive signals 57 computed during the setup process. Therefore the computation of error functions in block 60, the resulting update of drive signals 61 and feedback loop 62 would be omitted. Control microphones C1-Cn would therefore perform only a monitoring function.

Vibro-acoustic controller 12 may be any controller capable of performing the functions of the controller listed above. Controller 12 generally includes a processor and a graphical user interface (not shown), as known to those of ordinary skill in the art. In an embodiment, controller 12 may be an existing mechanical vibration controller such as, by way of example and not of limitation, the Spectral Dynamics Jaguar system.

In the embodiment shown and described with respect to FIGS. 1-3 there are n=12 control microphones C1-C12 and m=12 transducer groups T1-T12. However, those of ordinary skill in the art recognize that more or less control microphones and transducer groups may be utilized. For example, and not by way of limitation, the number of control microphones may be in the range of one to sixteen and the number of separately driven transducer groups may be in the range of four to sixteen. However, those of ordinary skill in the art recognize that additional control microphones and separately driven transducer groups may be utilized depending on the unit under test and the limits of controller 12. The band-width of the individual frequency bands of the power spectral density data used to represent the acoustical input signals and acoustical reference spectrum data is preferably equal to or less than 12.5 Hz and may be any suitable narrow band-width as determined by the characteristics of the available FFT functions such as and by way of example; 6.25 Hz, 3.125 Hz, 2.5 Hz, 1.25 Hz or 0.625 Hz.

Figure 4:
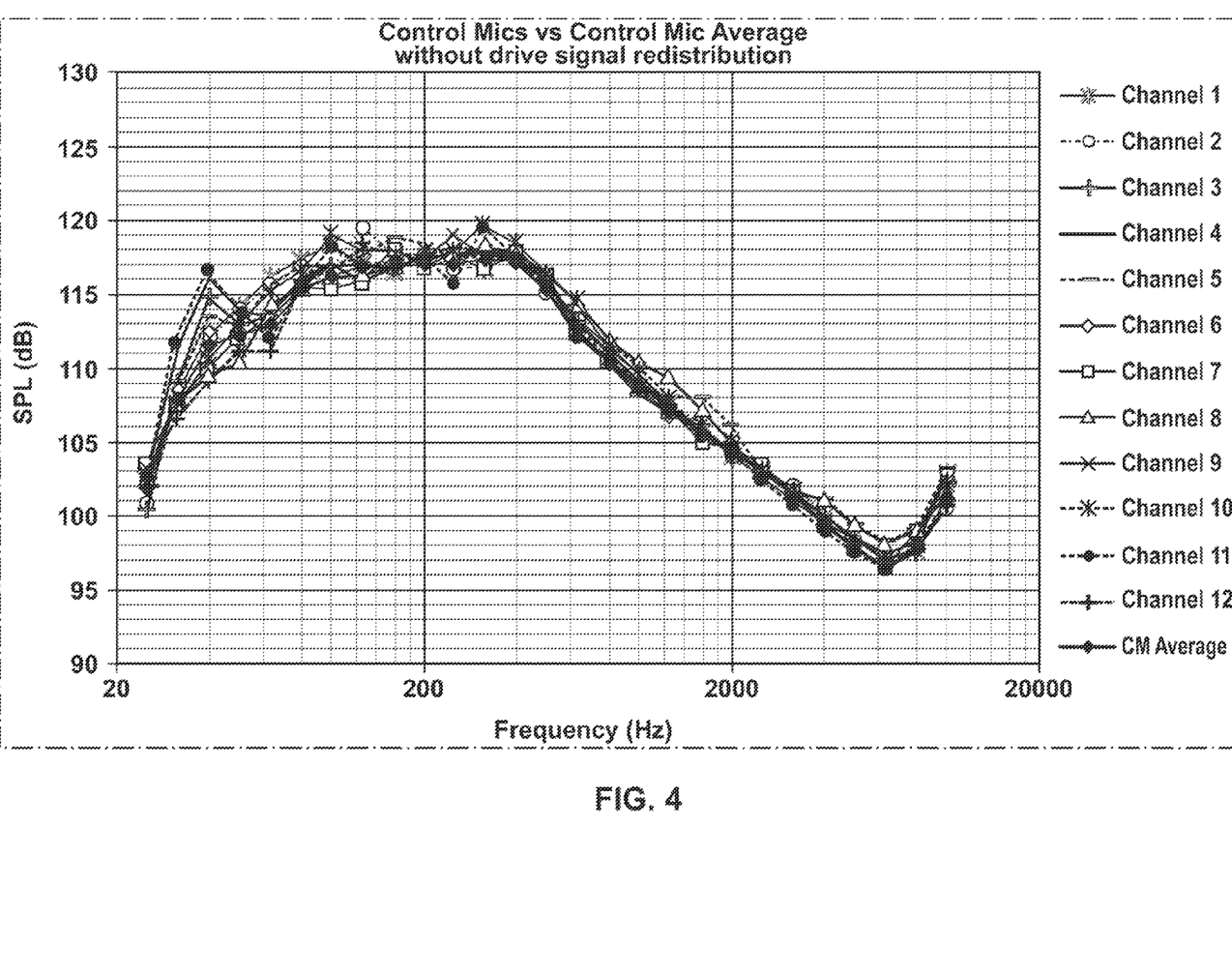
FIG. 4 is a diagram showing measured spectral variation of sound pressure for control microphones versus the average of all control microphones for the system of FIGS. 1, 2 and 3 employing MIMO control with twelve control microphones and twelve separate outputs driving twelve acoustic sources.

Referring to FIG. 4 there is shown actual measured data for spectral variation at each control microphone position for a DFAT system in accordance with an embodiment according to the '870 application employing multiple-input-multiple-output (MIMO) control with twelve control microphones and twelve separate outputs driving twelve acoustic sources as compared to the average of all control microphones. As can be seen from inspection there is relatively little variation between individual control microphones and little deviation from the average of all control microphones.

Figure 5:
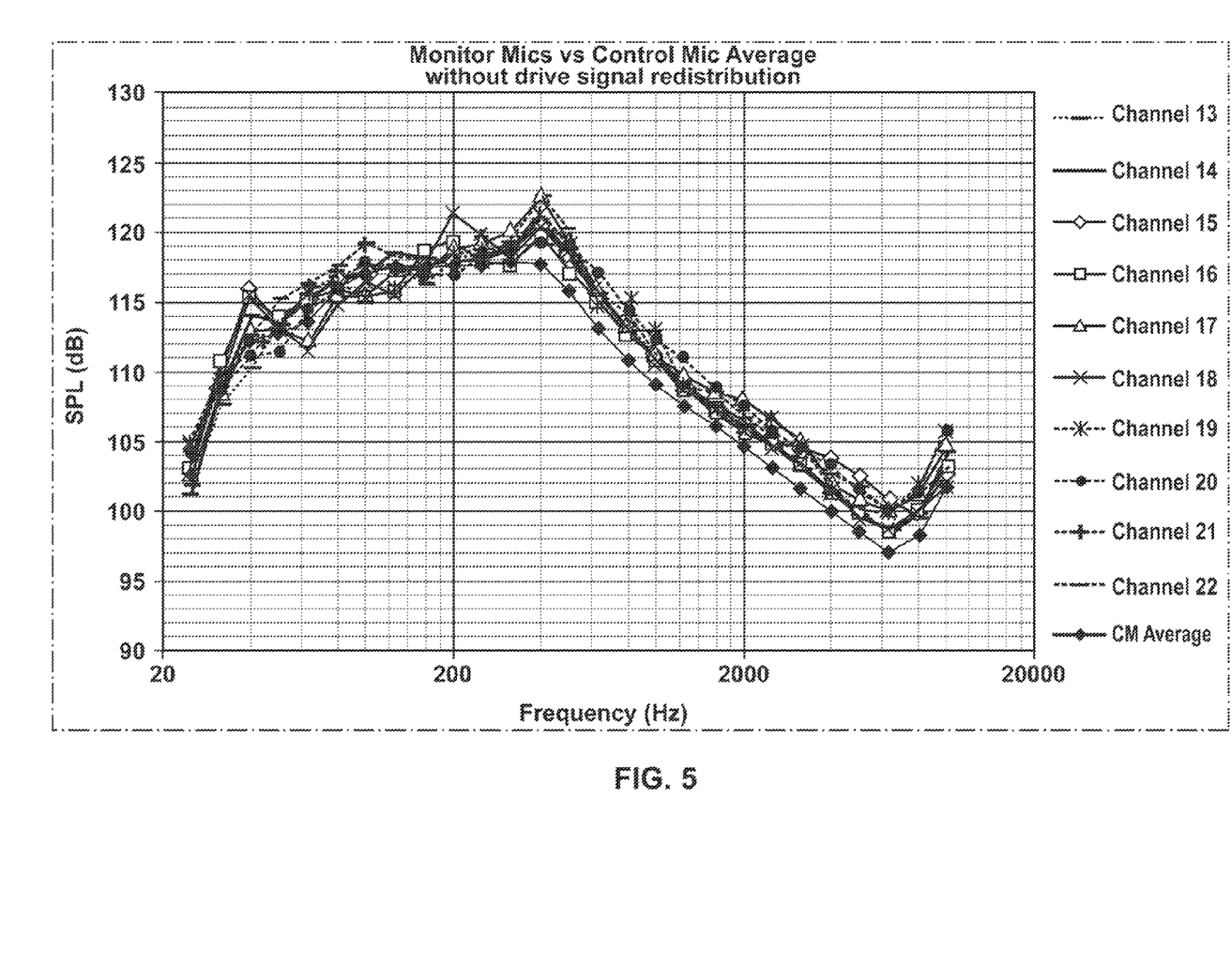
FIG. 5 is a diagram showing measured spectral variation of sound pressure for monitor microphones versus the average of all control microphones for the system of FIGS. 1, 2 and 3 employing MIMO control with twelve control microphones and twelve separate outputs driving twelve acoustic sources.

Referring to FIG. 5 there is shown actual measured data for spectral variation at each of ten monitor microphones located at non-control positions for a DFAT system in accordance with an embodiment according to the '870 application employing multiple-input-multiple-output (MIMO) control with twelve control microphones and twelve separate outputs driving twelve acoustic sources as compared to the average of all control microphones. As can be seen from inspection there is greater variation between individual monitor microphones and greater deviation from the average of control microphones than for the control microphones themselves. In addition the data shows a generally greater acoustic intensity above approximately 150 Hz for the non-control monitor locations as compared to the average of the control microphones.

Figure 6:
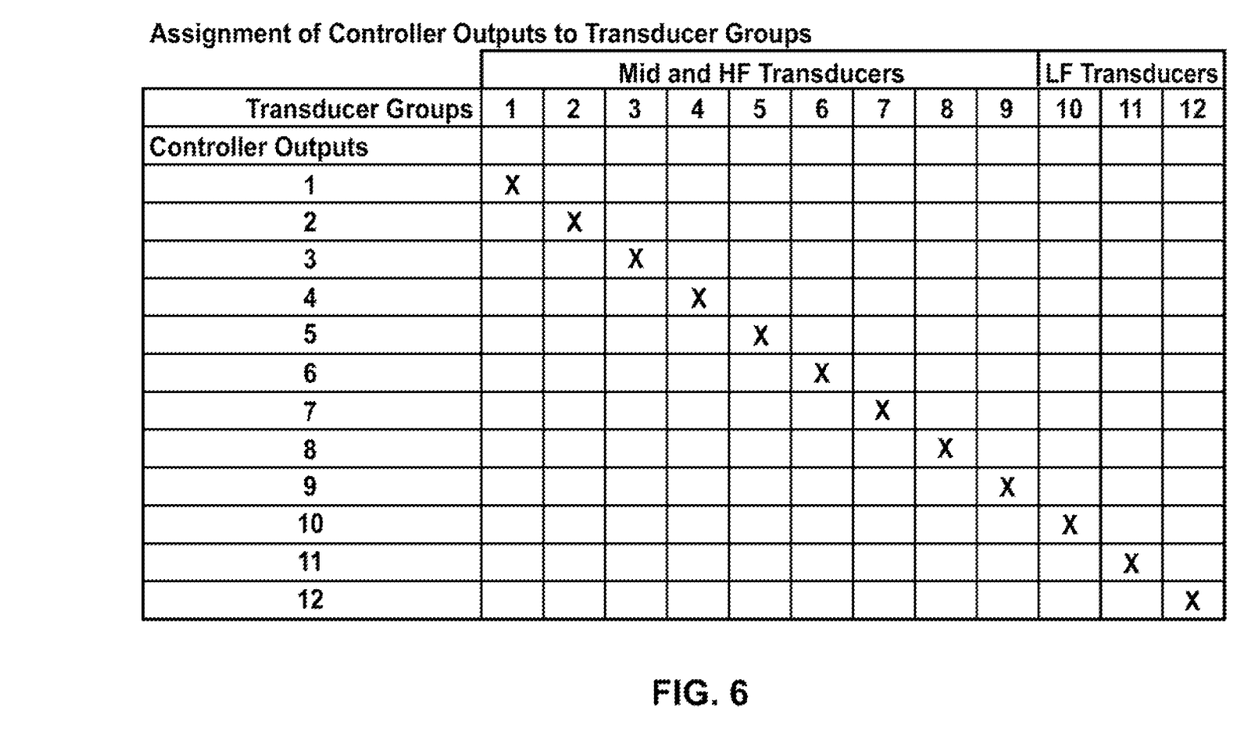
FIG. 6 is a diagram showing the assignment of separately controllable control output signals to transducer groups for the system of FIGS. 1, 2 and 3 employing MIMO control with twelve control microphones and twelve separate outputs driving twelve acoustic sources.

Referring to FIG. 6 there is shown the assignment of controller output signals to transducer groups in accordance with the '870 application. As can be seen from inspection there is a one to one correspondence between separately controllable controller output signals and transducer groups.

Figure 7:
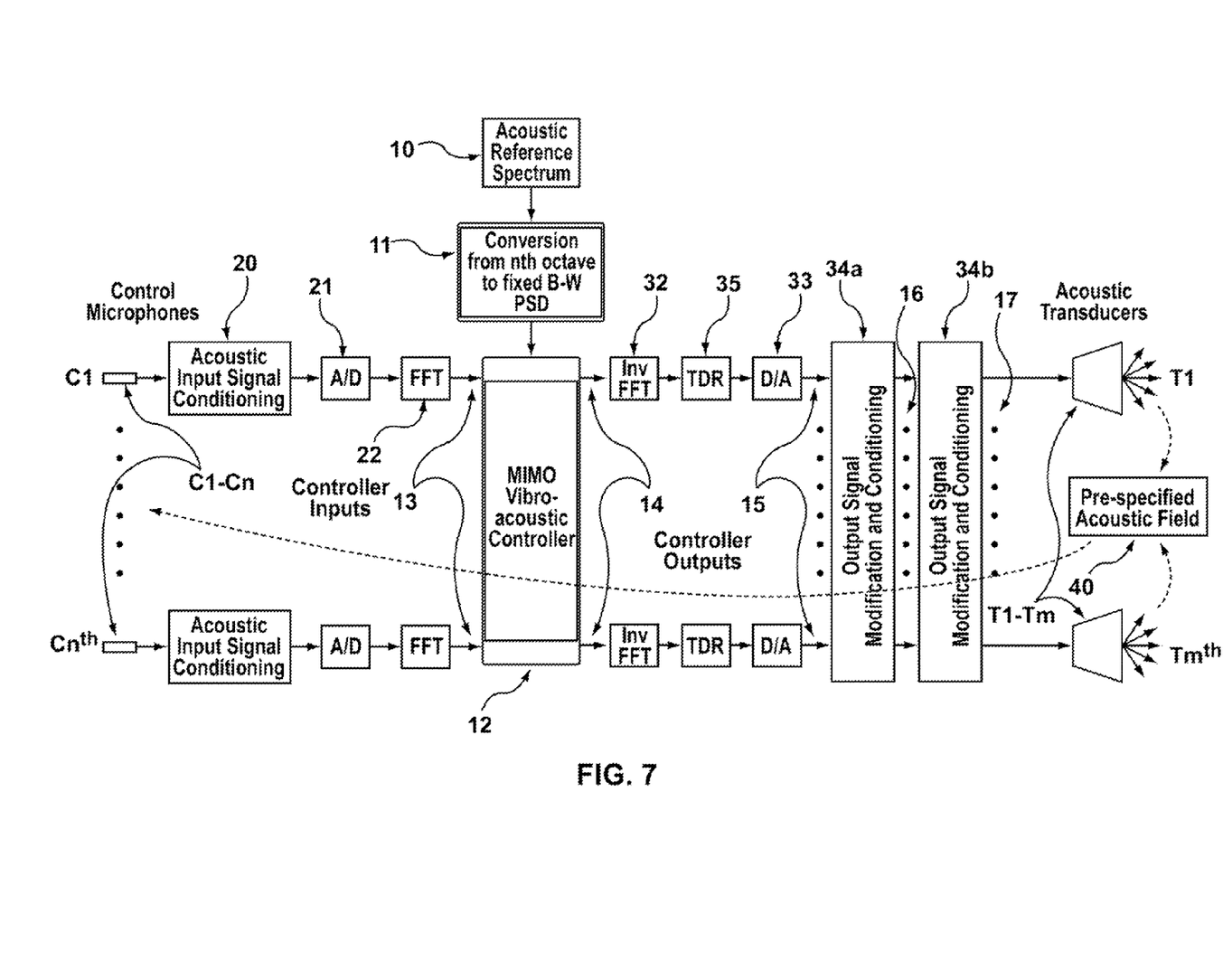
FIG. 7 is simplified block diagram of a direct field acoustic testing system according to an embodiment of the present invention.

Referring to FIG. 7, there is shown a simplified block diagram in accordance with an embodiment hereof. Features are as described for FIG. 2 and are marked with the same reference numbers excepting that in FIG. 7 output signal conditioning means 34 of FIG. 2 has been replaced with output signal modification and combination means 34a, and signal conditioning means 34b. After passing through digital to analog convertors 33 output signal modification and combination means 34a creates a secondary group of output signals 16 each of which is a combination of one or more of the separately controllable controller output signals 15. Each secondary output signal 16 is then conditioned in output signal conditioner 34b according to the input requirements of the amplification and acoustical transducers T1-Tm. By way of example and not of limitation, the conditioning may include additional filtering, gain, attenuation or power amplification. Each of the conditioned signals is then applied to the respective acoustical transducer group, T1-Tm. By way of example and not of limitation, output signal modification and combination means 34a may create said secondary output signals 16 by attenuating, amplifying, filtering, delaying, adding, subtracting, correlating or any other manipulation of separately controllable controller output signals 15 so as to create appropriate combinations of signals for each group of transducers.

In this FIG. 7 according to this embodiment hereof the modification and combination means 34a may for example be any suitable matrix switch or mixer or digital signal processor (DSP) unit such as the RANE RPM-88 or Yamaha DME64N. Additionally the modification and combination means 34a need not be a separate unit. Referring to FIG. 7 there is shown just one of many possible positions in the signal path for the performance of the modification and combination function. As will be immediately apparent to anyone with ordinary skill in the art this function may be accomplished at any point in the signal path after the development of individually controllable output signals whether in analog or digital form. By way of example and not of limitation, such signal combination may be integrated into the controller 12 itself or integrated into the final signal conditioning means 34b.

Figure 8:
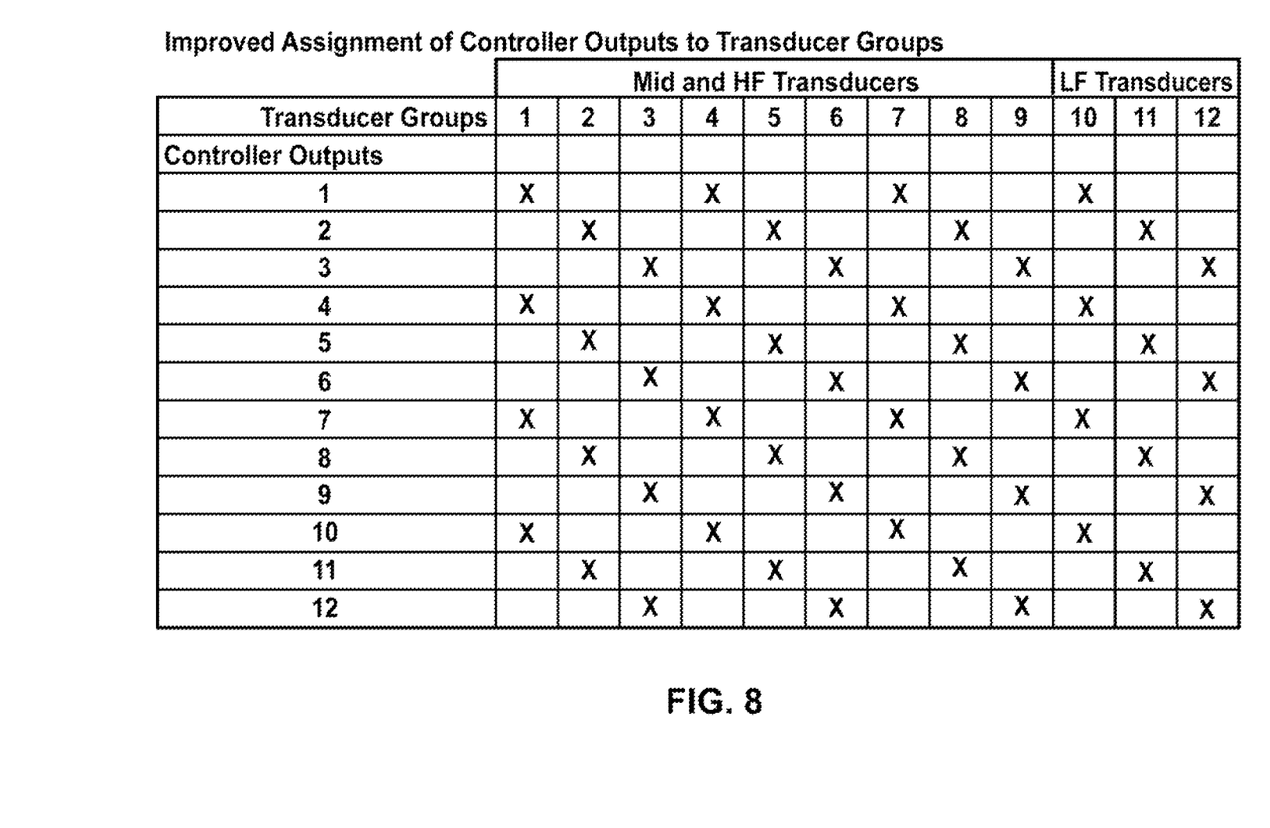
FIG. 8 is a diagram showing the assignment of separately controllable control output signals to transducer groups according to an embodiment hereof employing MIMO control with twelve control microphones and twelve separate outputs driving twelve acoustic sources.

Referring to FIG. 8, in one specific embodiment hereof employing multiple-input-multiple-output (MIMO) control with twelve control microphones and twelve separately controllable controller outputs the separately controllable controller output signals 15 of FIG. 7 are combined according to FIG. 8 to form secondary output signals for the respective acoustical transducer groups. By inspection we can see that secondary output 16-1 is composed of separately controllable controller output signals 15-1, 15-4, 15-7 and 15-11 added equally together. Secondary output 16-2 is composed of separately controllable controller output signals 15-2, 15-5, 15-8 and 15-12 added equally together and similarly for secondary outputs 16-3 through 16-12 according to FIG. 8.

Figure 9:
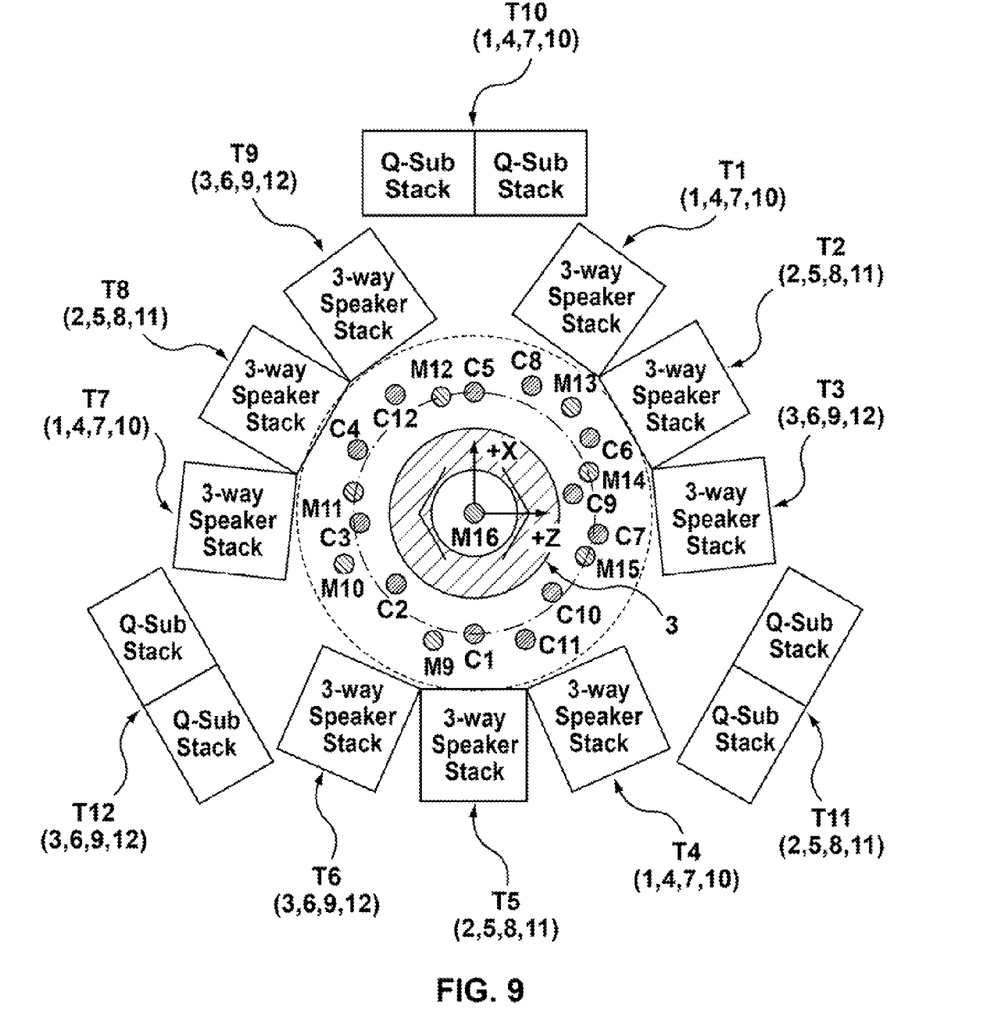
FIG. 9 schematic layout of an acoustical transducer group and controller output assignments for direct field acoustic testing according to an embodiment hereof employing MIMO control with twelve control microphones and twelve separate outputs driving twelve acoustic sources.

Referring to FIG. 9 there is shown the transducer arrangement and signal composition according to this embodiment hereof with twelve control microphones, twelve separately controllable controller outputs and twelve groups of acoustical transducers. Each acoustical transducer group T1 through T12 is shown followed by the combination of separately controllable controller output signals being directed to that group of transducers in parentheses. As can be seen from inspection of the figure, each separately controllable controller output signal 15 of FIG. 7 is distributed to at least one of the low frequency transducer groups T10-T12 and to at least three of the upper frequency transducer groups T1-T9 in such a way that with regard to the upper frequency transducer groups T1-T9 each separately controllable controller output signal 15 is distributed substantially evenly around the circle.

Figure 10:
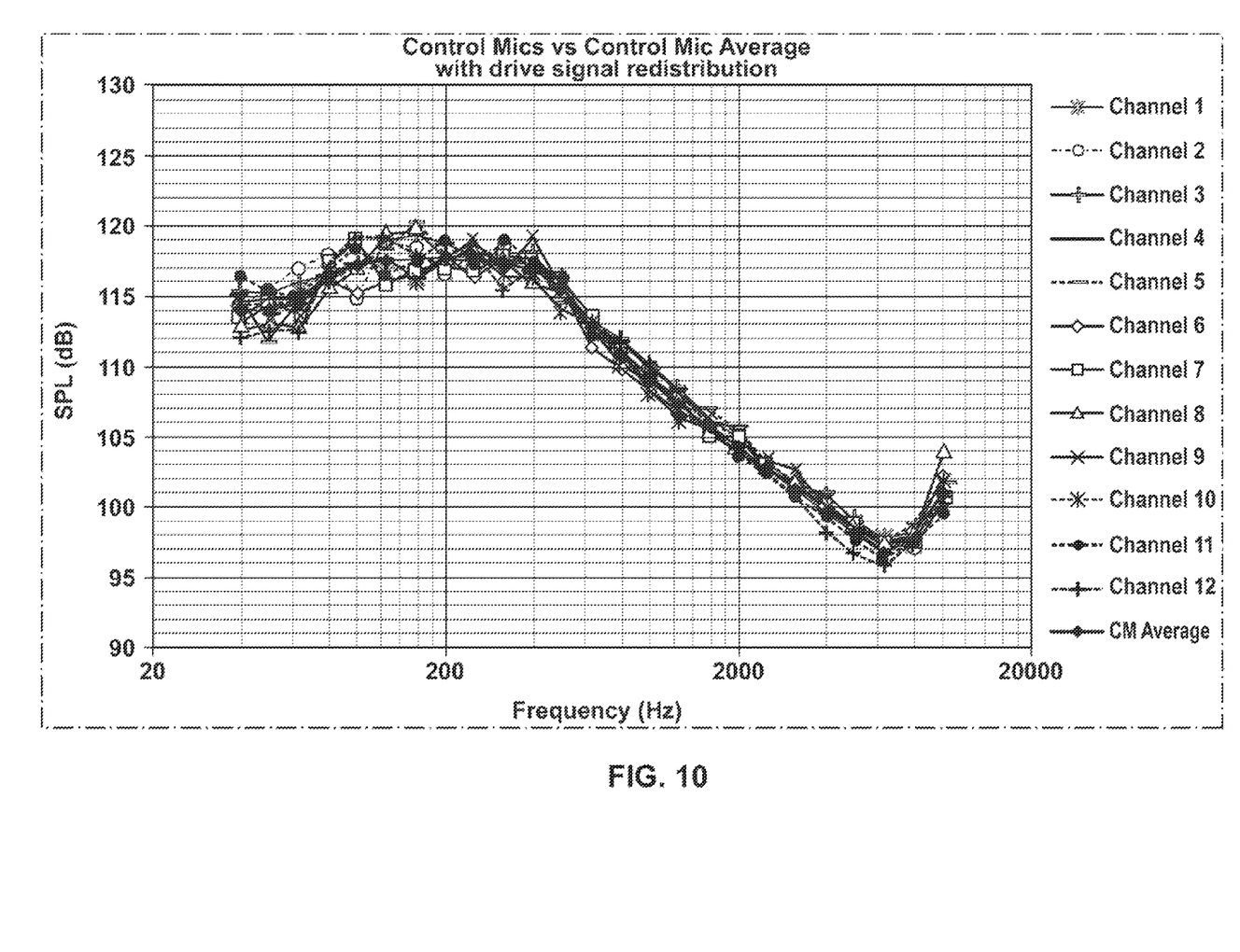
FIG. 10 is a diagram showing measured spectral variation of sound pressure for control microphones versus the average of all control microphones for an embodiment hereof employing MIMO control with twelve control microphones and twelve separate outputs driving twelve acoustic sources.

Referring to FIG. 10 there is shown actual measured data from this embodiment hereof with twelve control microphones, twelve separately controllable controller outputs and twelve groups of acoustical transducers which compares the spectral magnitude of each control microphone to the average of all control microphones. As can be seen from inspection there is relatively little variation between individual control microphones and little deviation from the average of all control microphones.

Figure 11:
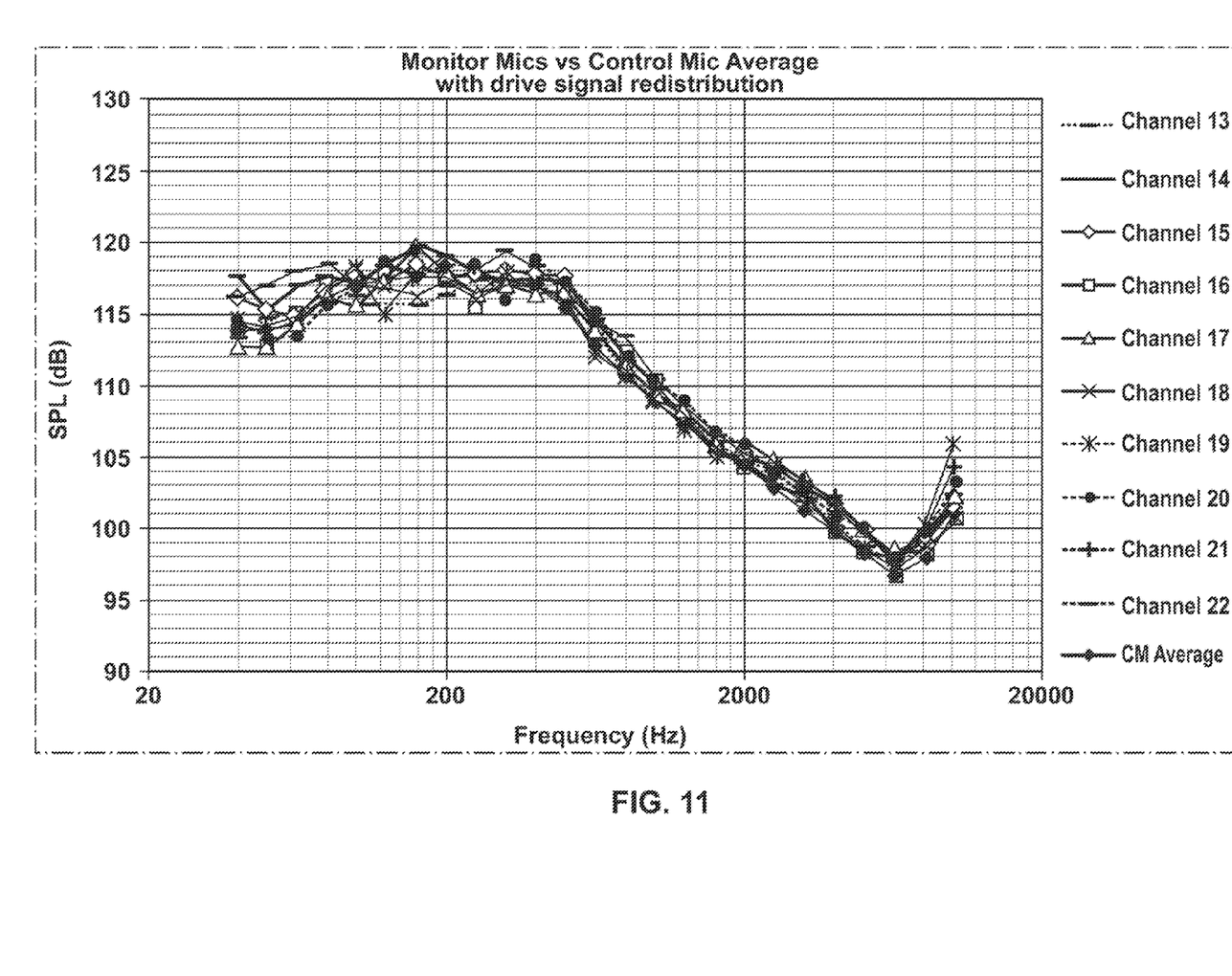
FIG. 11 is a diagram showing measured spectral variation of sound pressure for monitor microphones versus the average of all control microphones for an embodiment hereof employing MIMO control with twelve control microphones and twelve separate outputs driving twelve acoustic sources.

Referring to FIG. 11 there is shown actual measured data from this embodiment hereof employing multiple-input-multiple-output (MIMO) control with twelve control microphones, twelve separately controllable controller outputs and twelve groups of acoustical transducers which compares the spectral magnitude of each of ten monitor microphones located at non-control positions to the average of all control microphones. As can be seen from inspection there much less variation between individual monitor microphones and much less deviation from the average of all control microphones as compared to the system data shown in FIG. 5.

Referring to FIG. 1 it can be seen by inspection that the acoustic field at each control microphone C1-C8 is influenced primarily by the acoustic transducers or transducer groups T1-T12 nearest to each control microphone and significantly less influenced by transducers further away. As will be apparent to those with ordinary skill in the art the contribution to the acoustic field at a point in space from a given acoustic source drops rapidly as the distance to that acoustic source increases. By way of example and not of limitation and referring to FIG. 1 it can be seen by inspection that the acoustic field at control microphone C4 will be dominated by the output of acoustic transducer groups T8 and T9. More distant acoustic transducer groups for example T1, T10 or T7 will have much less influence on the acoustic field at control microphone C4. Therefore, it is possible to achieve a pre-specified acoustic field at each of the control microphones C1-08 principally by modifying the output of the transducer groups T1-T12 nearest to each control microphone C1-C8. Modification of more distant transducer groups will have little effect on the acoustic field of the control microphones. Referring to FIG. 6 from inspection of the one to one correspondence between separately controllable controller outputs 1-12 and acoustic transducer groups T1-T12 it can be seen that modification of the output of each transducer group requires modification of just one controller output signal. Therefore, the acoustic field at each control microphone will depend almost entirely on variations in only a few of the separately controllable controller outputs, typically three or less and often only one. In addition, and referring to FIG. 1, it can be seen from inspection that the transducer groups which principally determine the acoustic field for one or two control microphones will have little effect on more distant control microphones. Therefore the controller outputs operatively coupled to the transducer groups which principally determine the acoustic field for a given control microphone will have little effect on the acoustic field at more distant control microphones. By way of example and not of limitation and referring to FIG. 1 and FIG. 6, it can be seen by inspection that the acoustic field at control microphone C4 will be principally determined by transducer groups T7-T9 which are operatively coupled to controller outputs 7-9. It can also be seen from inspection that transducer groups T1-T6 and T10-T12 and therefore controller outputs 1-6 and 10-12 will have little effect on the acoustic field at control microphone C4. This can lead to deviations from the pre-specified acoustic field at points in space between the control microphones.

Referring to FIG. 9 in accordance with an embodiment of the current invention it can be seen from inspection that the acoustic field at each control microphone C1-C12 is still principally determined by the nearest transducer groups. However, and referring also to FIG. 8, each transducer group T1-T12 now receives a combination of controller output signals as shown in parentheses. Therefore, the acoustic field at each control microphone is now principally determined by variations in a combination of controller output signals. Additionally, variations in those same controller outputs also principally determine acoustic fields at other control microphone locations. By way of example and not of limitation and referring to FIG. 9 and FIG. 8, the acoustic field of control microphone C4 is principally determined by transducer groups T7-T9. However, the acoustic output of transducer groups T7-T9 is determined by variations in all controller outputs 1-12. Similarly, the acoustic field at a control microphone C6, at some distance from C4, will be principally determined by transducer groups T1-T3 which also respond collectively to variations in controller outputs 1-12 resulting in reduced deviations from the pre-specified acoustic field at points in space between the control microphones.

Referring to FIG. 9 by way of example and not of limitation, it can be seen from inspection of the figure that controller output signals are combined and distributed to transducer groups such that the influence of variations in each controller output is distributed more or less symmetrically around the unit under test. However, it will be readily apparent that many different arrangements are possible, symmetrical or asymmetrical, uniform or non-uniform, which fall within the scope of this invention. In general, a correlation has been demonstrated between the coherence of the acoustic field around the unit under test and the amount of the influence of variations of each controller output on the acoustic field at each control microphone. Greatest coherence corresponds to the case wherein variations of all controller outputs have the same influence on the acoustic field at all control microphones while least coherence corresponds to the case where variations of each controller output principally influence the acoustic field at just one control microphone.

It will also be readily apparent that an endless variety of combinations of separately controllable controller output signals may be created for the purpose of achieving an acoustic field which has a higher degree of uniformity or which conforms more closely to a pre-specified acoustic field all of which fall within the scope of this invention. By way of example and not of limitation, said acoustic field specifications may include acoustic intensity gradients or other field asymmetries as required for the specific test. Additionally, separately controllable controller output signals need not be combined solely through simple addition and need not all be combined in the same proportion. By way of example and not of limitation, they may be amplified, attenuated, filtered, delayed or otherwise modified relative to the other separately controllable controller output signals with which they are being combined through addition, subtraction, multiplication, division, cross-correlation or any other form of operation. The arrangement of transducers need not be circular and may be any arrangement suitable for achievement of the test specifications with a specific UUT. By way of example and not of limitation, such arrangements may include any portion of a sphere, rectangular in plan, oblate and may or may not include overhead transducers. It will also be apparent to those of ordinary skill in the art that many more variations may be implemented which fall within the scope of the present invention. These may include by way of example and not of limitation; differing types or numbers of transducers, differing numbers of inputs and outputs, different transducer array layouts, alternate configurations or connections of transducer sub-arrays to said outputs, choices of locations for control or monitoring, any suitable type of multiple-input-multiple-output control system or logic, different types of or combinations of signals for use during operation, or any other circumstances in which the disclosed multiple output techniques are applied to a direct field acoustic testing system.

Referring to FIG. 6 there is shown the assignment of controller output signals to transducer groups in accordance with the '870 application. As can be seen from inspection there is a one to one correspondence between separately controllable controller output signals and transducer groups. Controller output signals 1-9 are assigned to Mid-HF transducer groups T1-T9 which generally reproduce frequencies above 100 Hz. Controller output signals 10-12 are assigned to low frequency transducer groups T10-T12 which generally reproduce frequencies from 20 Hz to 200 Hz. Referring to FIG. 3, a simplified block diagram which as previously discussed describes generally the functioning of one possible embodiment of a MIMO vibro-acoustic controller 12 is shown which is in accordance with the '870 application. As described in the '870 application, during closed loop operation, drive signals 1-*m* are continuously updated to maintain the pre-specified acoustic field. However, controller output signals 1-9 of FIG. 6 are assigned to transducer groups T1-T9 which reproduce frequencies generally above 100 Hz. As a result updated drive signals for transducer groups T1-T9 may include steadily increasing signal levels below 100 Hz. Controller output signals 10-12 of FIG. 6 are assigned to transducer groups T10-T12 which reproduce frequencies generally from 20 Hz to 200 Hz. As a result updated drive signals for transducer groups T10-T12 may include steadily increasing signal levels above 200 Hz. Increased signal levels at frequencies outside the intended frequency range for a group of transducers may lead to excessive power consumption, high distortion, failure to achieve the pre-specified acoustic field characteristics or failure of system components. Referring to FIG. 9, upper frequency transducer groups T1-T9 are shown which reproduce frequencies generally above 100 Hz and low frequency transducer groups T10-T12 are shown which reproduce frequencies generally from 20 Hz to 200 Hz. Each acoustical transducer group T1 through T12 is shown followed by the combination of separately controllable controller output signals being directed to that group of transducers in parentheses. As can be seen from inspection of the figure, each separately controllable controller output signal 15 of FIG. 7 is distributed to at least one of the low frequency transducer groups T10-T12 and at least one of the upper frequency transducer groups T1-T9 such that variations in each separately controllable controller output signal cause variations in the acoustic output of a combination of transducer groups which collectively reproduce frequencies covering the entire acoustic frequency range of the pre-specified acoustic field. Accordingly, updated drive signals for transducer groups controlled by each separately controllable controller output signal do not contain frequency content outside the intended acoustic frequency range. By way of example and not of limitation, the number of different transducer groups covering different acoustic frequency ranges may be between two and eight. It will be apparent to those of ordinary skill in the art that many such signal distribution arrangements are possible for assigning each separately controllable controller output signal to groups of transducers such that variations in each separately controllable controller output signal cause variations in the acoustic output of a combination of transducer groups which collectively reproduce frequencies covering the entire acoustic frequency range of the pre-specified acoustic field. All such arrangements are within the scope of this invention.

As used herein, the term "different frequency ranges" may include overlapping frequency ranges. For example, and not by way of limitation, it has been described above that transducer groups T1-T9 reproduce frequencies generally above 100 Hz and transducer groups T10-T12 reproduce frequencies between 20 and 200 Hz. Accordingly, transducer groups T1-T9 reproduce a different frequency range than transducer group T10-T12 even though the frequency ranges may overlap in the 100-200 Hz range. It will be apparent to those of ordinary skill in the art that different frequency ranges reproduced by separate groups of acoustical transducers for the purpose of reproducing a broader overall frequency range typically have some overlap. All such overlapping frequency ranges also fall within the scope of this invention.

What is claimed is:

1. A direct field acoustic testing system comprising:
   a control microphone;
   a controller operatively coupled to the control microphone such that the controller receives at least one input signal from the control microphone and provides at least four separately controllable controller output signals;
   a combiner configured to combine said at least four separately controllable controller output signals to form at least four secondary output signals, at least one of the at least four secondary output signals composed of a combination of at least two of said at least four separately controllable controller output signals; and
   at least four acoustic transducers or groups of transducers each of which is operatively coupled to at least one of said at least four secondary output signals such that the output of at least one of the at least four acoustic transducers or transducer groups varies in response to changes in at least two of the at least four separately controllable controller output signals.

2. The direct field acoustic testing system of claim 1 wherein the at least four acoustic transducers or transducer groups are generally arranged to provide direct field acoustic excitation to all sides of a unit under test when viewed in plan such that the acoustic transducers or transducer groups operatively coupled to each of said at least four secondary output signals are distributed substantially evenly around the device under test.

3. The direct field acoustic testing system of claim 1, wherein the combiner is a matrix switch, a mixer, or a digital signal processor unit.

4. The direct field acoustic testing system of claim 1, wherein the control microphone comprises at least four control microphones.

5. The direct field acoustic testing system of claim 1, wherein the combiner combines said at least four separately controllable output signals by attenuating, amplifying, filtering, delaying, adding, subtracting, correlating or any other manipulation of said at least four separately controllable output signals.

6. The direct field acoustic testing system of claim 1, further comprising a conditioner configured to condition said at least secondary output signals according to input requirements of the at least four acoustic transducers or groups of transducers such that each of the at least four acoustic transducer or groups of transducers is coupled to at least one of the at least four secondary output signals after conditioning.

7. The direct field acoustic testing system of claim 6, wherein the conditioner provides additional filtering, gain, attenuation or power amplification of said at least four secondary output signals.

8. A direct field acoustic testing system comprising:
a control microphone;
a controller operatively coupled to the control microphone such that the controller receives at least one input signal from the control microphone and provides at least four separately controllable controller output signals;
a combiner configured to combine said at least four separately controllable controller output signals to form at least four secondary output signals each composed of combinations of at least two of said at least four separately controllable controller output signals; and
at least four acoustic transducers or groups of transducers each of which is operatively coupled to at least one of said at least four secondary output signals, wherein at least one of the four acoustic transducers or groups of transducers covers a first frequency range and at least one of the four acoustic transducers or groups of transducers covers a second frequency range different from the first frequency range, wherein the combiner combines the at least four separately controllable controller output signals such that each of the at least four separately controllable controller output signals is operatively connected to at least one of the acoustic transducers or groups of transducers covering the first frequency range and to at least one of the acoustic transducers or groups of transducers covering the second frequency range.

9. The direct field acoustic testing system of claim 8 wherein the at least four acoustic transducers or transducer groups are generally arranged to provide direct field acoustic excitation to all sides of a unit under test when viewed in plan such that the acoustic transducers or transducer groups operatively coupled to each of said at least four secondary output signals are distributed substantially evenly around the unit under test.

10. A direct field acoustic testing system comprising:
twelve control microphones;
a controller operatively coupled to the control microphones such that the controller receives twelve input signals, one from each of the control microphones, and provides twelve separately controllable controller output signals;
a combiner configured to combine the twelve separately controllable output signals to form twelve secondary output signals each composed of combinations of at least two of the twelve separately controllable controller output signals; and
twelve acoustic transducers or groups of transducers each of which is operatively coupled to at least one of the twelve secondary output signals such that the output of each transducer or transducer group varies in response to changes in at least two of the twelve separately controllable controller output signals.

11. The direct field acoustic testing system of claim 10, wherein the twelve transducers or transducer groups are arranged around a unit under test, wherein nine of the twelve transducer or transducer groups are three-way electro-dynamic loudspeaker systems generally covering the frequency range above 100 Hz and three of the twelve transducer or transducer groups are electro-dynamic subwoofer loudspeakers generally covering the frequency range from 20 Hz to 200 Hz.

12. The direct field acoustic testing system of claim 11, wherein each of the twelve separately controllable controller output signals is operatively coupled to at least one of the nine transducers or transducer groups covering the frequency range above 100 Hz and to at least one of the three transducer or transducer groups covering the frequency range from 20 Hz to 200 Hz.

13. The direct field acoustic system of claim 10, wherein at least one of the twelve acoustic transducers or transducer groups cover a first frequency range and wherein at least two of the twelve acoustic transducers or transducer groups cover a second frequency range different from the first frequency range, and wherein each of the twelve separately controllable controller output signals is operatively coupled to at least one of the acoustic transducers or transducer covering the first frequency range and to at least one of the acoustic transducers or transducer covering the second frequency range.

* * * * *